United States Patent [19]
Mölter et al.

[11] Patent Number: 6,067,865
[45] Date of Patent: *May 30, 2000

[54] METHOD AND DEVICE FOR DETERMINING PARTICLE SIZE DISTRIBUTION IN AEROSOL

[75] Inventors: Leander Mölter, Wörth; Friedrich Munzinger, Gondelsheim, both of Germany

[73] Assignee: Palas GmbH Partikel-und LasermeBtechnik, Karlsruhe, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/985,250

[22] Filed: Dec. 4, 1997

Related U.S. Application Data

[63] Continuation-in-part of application No. 08/890,998, Jul. 10, 1997, abandoned.

[51] Int. Cl.[7] .................................................. G01N 21/05
[52] U.S. Cl. .......................................................... 73/865.5
[58] Field of Search ........................... 73/865.5; 356/335, 356/336, 440–442, 438; 324/71.4

[56] References Cited

U.S. PATENT DOCUMENTS

| | | | |
|---|---|---|---|
| 4,110,043 | 8/1978 | Eisert | 356/336 |
| 4,318,180 | 3/1982 | Lundquist et al. | 364/555 |
| 4,444,500 | 4/1984 | Flinsenberg et al. | 356/336 |
| 4,525,666 | 6/1985 | Groves | 324/71.4 |
| 4,966,462 | 10/1990 | Novick | 356/336 |
| 5,185,641 | 2/1993 | Igushi et al. | |
| 5,641,919 | 6/1997 | Dahneka | 73/865.5 |
| 5,679,907 | 10/1997 | Ruck | 73/865.5 |

FOREIGN PATENT DOCUMENTS

| | | |
|---|---|---|
| 0485817 | 5/1992 | European Pat. Off. . |
| 4341573 | 3/1995 | Germany . |
| 56-058636 | 5/1981 | Japan . |
| 1020432 | 1/1989 | Japan . |
| 02451 | 9/1989 | Japan ................. 73/865.5 |

*Primary Examiner*—Robert Raevis
*Attorney, Agent, or Firm*—Antonelli, Terry, Stout & Kraus, LLP

[57] ABSTRACT

To increase the dynamic range when testing the particle size distribution of aerosols, the invention proposes a method whereby particles are detected in two measuring volumes connected in series in the measuring channel, whereby in particular the total number of particles flowing through the measuring channel passes through one measuring volume while only a smaller number of particles passes through the other measuring volume. A device appropriate therefor provides for a first measuring volume (MV1) to be located immediately downstream of an inlet nozzle (4) for the aerosol and having a surface perpendicular to the flow direction of the aerosol, said surface corresponding to the surface of the end of the inlet nozzle and for a second measuring volume to be provided downstream of the first measuring volume at a distance therefrom, the cross section of said second measuring volume perpendicular to the flow direction of the aerosol being smaller than the cross section of the measuring channel.

20 Claims, 2 Drawing Sheets

METHOD AND DEVICE FOR DETERMINING PARTICLE SIZE DISTRIBUTION IN AEROSOL

CROSS-REFERENCE TO RELATED APPLICATION

This is a Continuation-in-Part Application of United States Ser. No. 08/890,998, filed Jul. 10, 1997, now abandoned, which application is incorporated herein by reference in its entirety.

The invention relates to a method for testing particle size distribution in aerosols by detecting particles moving through a measuring volume and a device for testing particle size distribution in aerosols, with a measuring channel conducting the aerosol to be investigated.

Thus far it has only been possible to use a device for testing particle size distribution in aerosols to investigate particles with a particle concentration in a narrow range of concentration variation. Hence it was not possible in practice to investigate aerosols in which the concentrations varied widely as a function of time precisely and exactly in all concentration ranges encountered.

Hence the goal of the invention is to provide a method and device for testing particle size distribution in aerosols that covers a greater dynamic range of particle concentrations.

According to the invention, this goal is achieved in a method of the type referred to above by detecting particles in two measuring volumes arranged in series in the measuring channel, with the total number of particles flowing through the measuring channel passing through one measuring volume and only a small number of particles passing through the other measuring volume. For achieving the goal, a device according to the invention provides that a first measuring volume is located immediately downstream of an inlet nozzle for the aerosol and has one surface perpendicular to the flow direction of the aerosol, said surface corresponding to the surface where the inlet nozzle ends and a second measuring volume is provided downstream of the first measuring volume and at a distance therefrom, the cross section of said second measuring volume perpendicular to the flow direction of the aerosol being smaller than the cross section of the measuring channel.

The measures according to the invention make it possible considerably to increase the dynamic range of particle concentration in an aerosol, namely up to a range of practically zero particles/cm$^3$ to 10$^5$ or even 10$^6$ particles/cm$^3$ by detecting only a partial concentration range in each of the measuring volumes, namely a particle range of only up to approximately 5×10$^2$ particles/cm$^3$ in the first measuring volume, and measuring higher concentrations in the second measuring volume. Other concentration ranges can be covered by changing the cross section of the measuring volume.

Preferred embodiments of the method are characterized in that the measuring volumes are formed by the focal areas of the measuring beams in one of the measuring channels carrying the aerosol to be investigated and particularly in that the cross sections of the measuring beams in the focal areas are very different from each other. Accordingly the device is characterized in a further embodiment by measuring optics by means of which the measuring channel is illuminated by measuring beams, so that measuring volumes are formed in the measuring channel by the focal areas of the measuring beams. In addition, provision can be made such that the cross sections of the measuring beams in the focal areas are very different from each other.

Provision is made in the preferred embodiment for the cross sections of the measuring beams to differ from one another by at least a power of 10, especially with the cross section of the first measuring beam being greater than 10$^{-1}$ mm$^2$ in the focal range while the cross section of the second measuring beam is on the order of 10$^{-2}$ mm$^2$ in the focal range.

A particularly preferred embodiment provides for the total number of particles flowing through the measuring channel to pass through one measuring volume while only a small number of the particles passes through the other measuring volume.

In a particularly preferred further embodiment, provision is made for diluting the gas to be fed to the aerosol to be investigated, with the diluting gas being conducted in particular through an annular nozzle to the measuring channel, said nozzle surrounding an inlet nozzle conducting the aerosol to be investigated to the measuring channel. Other embodiments provide for the diluting gas to be conducted to the measuring channel in the area of the first measuring volume and/or the diluting gas to be conducted to the measuring channel in the area of the larger measuring volume.

While formerly the aerosol to be investigated was drawn through the measuring channel by suction, a preferred embodiment provides for the aerosol to be investigated to be carried by the diluting gas through the measuring channel.

The device according to the invention is characterized in preferred embodiments by a diluting channel terminating in the measuring channel and by a common radiation source for both measuring beams, with a beam splitter located downstream of the radiation source.

Further advantages and features of the invention will emerge from the claims and the description hereinbelow in which one sample embodiment of the invention is explained in detail with reference to the drawing.

Figure 1:
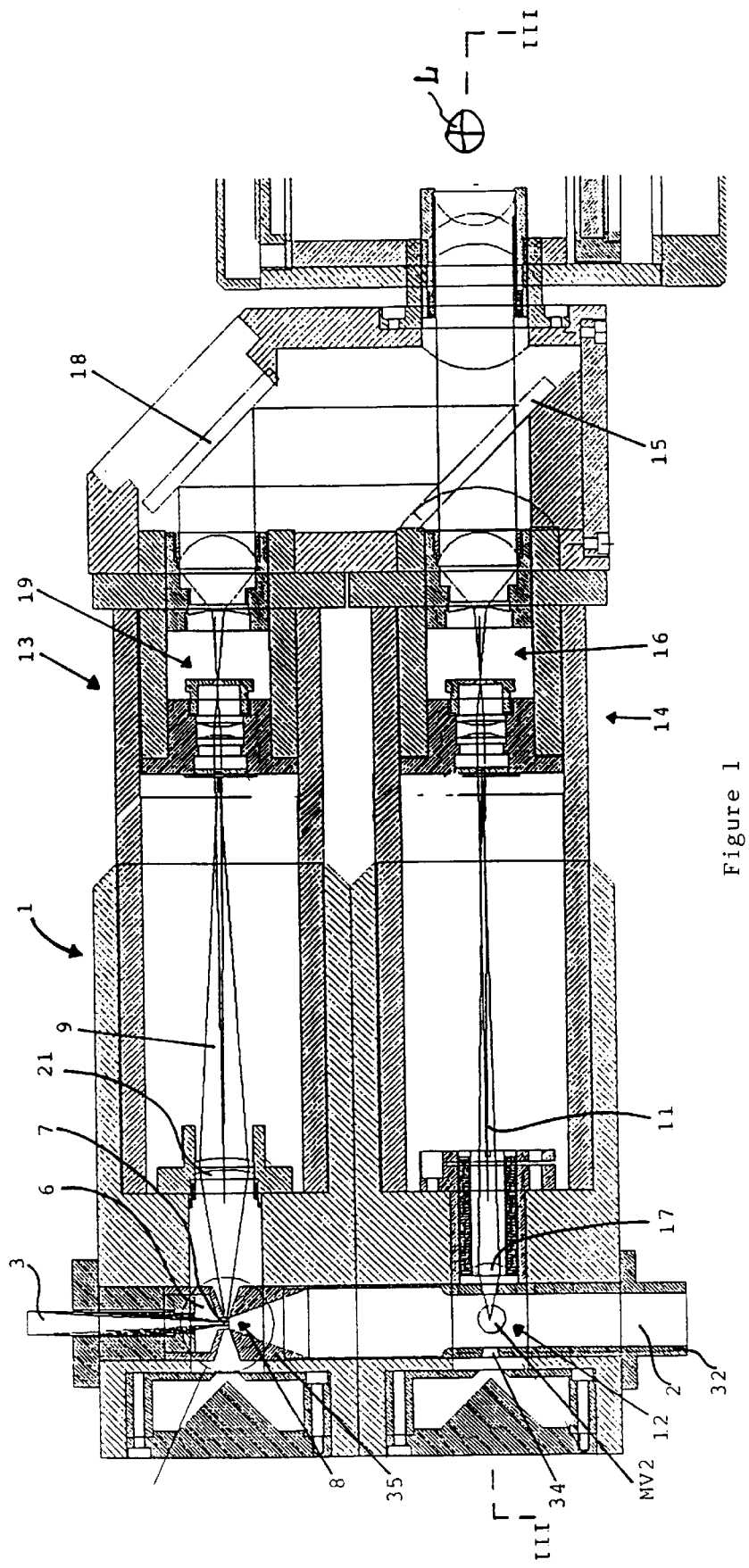
FIG. 1 is a device according to the invention in lengthwise section.
Figure 2:
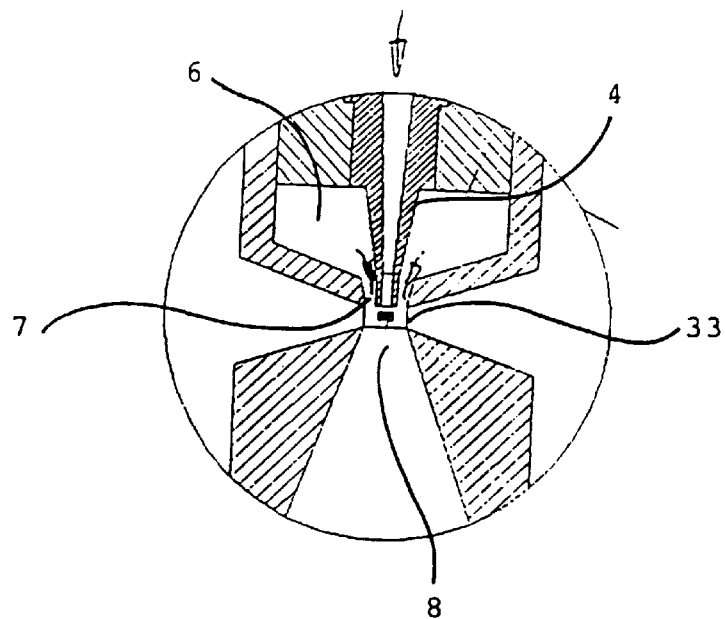
FIG. 2 is an enlarged representation of the supply area for the diluting air with the first measuring volume.

Device 1 according to the invention has a measuring channel 2. A supply channel for the aerosol with an inlet nozzle 4 terminates at the beginning of the measuring channel. Inlet nozzle 4 is surrounded by an annular channel 6 for diluting gas, said gas entering measuring channel 2 through an annular nozzle surrounding the outlet area of inlet nozzle 4. Immediately downstream of inlet nozzle 4 and annular nozzle 7 is a first focal area 8 of a first measuring beam 9 which forms a first measuring volume MV1. A second measuring beam 11 enters measuring channel 2 at a distance downstream from first measuring volume MV1, the focal area 12 of said measuring beam 11 forming a second measuring volume MV2 in the measuring channel. Measuring beams 9, 11 are produced by illuminating optics 13, 14 shown in FIG. 1. Illuminating optics 13, 14 have a common radiation source L. Radiation source L is preferably a white light source such as a high-pressure xenon lamp.

Radiation source L is located downstream of a half-silvered mirror 15, said mirror being followed by first imaging optics 16 through which a first part of the light-producing measuring beam 11 produced by radiation source L passes. Imaging optics 16 has lenses and diaphragms. A focusing lens 17 is disposed in the path of measuring beam 11 upstream of measuring channel 2, said lens focusing measuring beam 11 with a focal range in the middle of measuring channel 2.

The cross section of measuring beam 11 in focal area 12 is approximately $10^{-2}$ mm$^2$.

The portion of the beam of light from radiation source L reflected by half-silvered mirror 15 strikes a fully silvered mirror 18 aligned parallel to half-silvered mirror 15 so that the beam reflected by mirror 15 is parallel to measuring beam 11. Imaging optics 19 have lens diaphragms to generate measuring beam 9. This beam is focused by a lens 21 in its focal area 8 immediately upstream of inlet nozzle 7. Focal area 8 has a cross section of approximately 1 mm$^2$ and is thus one order of magnitude larger than focal area 12.

Figure 3:
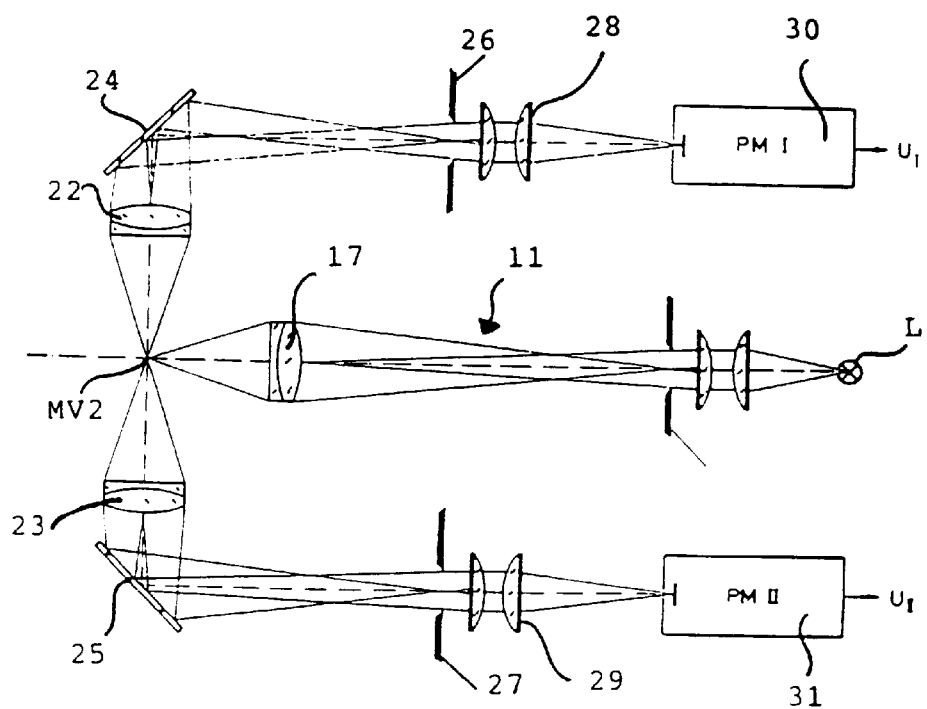
FIG. 3 is a cross section through FIG. 1 along line III—III.

The light reflected by the particles of the aerosol to be investigated perpendicular to the direction of measuring beams 9, 11 is detected by detecting optics as shown for measuring beam 11 and measuring volume MV2 in FIG. 3. Lenses 22, 23, mirrors 24, 25 followed by diaphragms 26, 27 and lens systems 28, 29 in front of detectors 30, 31 in the form of photomultipliers are provided on both sides of the measuring volume. The illuminating and detecting optics together form measuring optics for measuring volumes MV1 and MV2.

In the vicinity of measuring volumes MV1 and MV2, the tube forming channel 2 has transparent windows 33, 34. In the vicinity of the termination of inlet nozzle 4 and annular nozzle 7, measuring channel 2 tapers to a diameter corresponding to the diameter of annular nozzle 7 and flares continuously therefrom over a conical enlargement area 35.

The aerosol entering measuring channel 2 through inlet channel 3 and inlet nozzle 4 is carried along by the diluting gas supplied under pressure into annular space 6 and annular nozzle 7 through measuring channel 2 so that the diluting gas serves as a carrying agent. The aerosol to be investigated, still undiluted, is located in measuring volume MV1 immediately abutting the end of inlet nozzle 4 and formed by focal area 8. The mixture of the aerosol with the diluting gas and hence the dilution of the aerosol to be investigated takes place first in the abutting conically flaring area so that a diluted aerosol is then present in measuring volume MV2. Hence, low concentrations of less than 1, in particular 0.1 particles/cm$^3$, up to the order of magnitude of $10^2$, in particular $3 \times 10^2$ particles/cm$^3$ can be determined in measuring volume MV1. Each particle leaving the end of inlet nozzle 4 passes through measuring volume MV1 so that concentrations up to the aforesaid $3 \times 10^2$ particles/cm$^3$ can be measured. Such low concentrations would lead to great statistical uncertainty in measuring volume MV2, in which only a fraction of the total aerosol stream passing through measuring channel 2 is detected and analyzed.

Above $3 \times 10^2$ particles/cm$^3$, the concentration in the area of the measuring volume is too large and the radiation from the individual particles overlaps, so that the particles can no longer be detected individually by the detector. At high concentrations, the detector is in coincidence and can thus no longer count any particles. However, it is possible with monodispersed particles present in higher concentrations to switch the detectors associated with measuring volume MV1 (not shown in detail) to photometer mode (DC) and then determine the concentration at $10^6$ particles/cm$^3$ or even more.

Aerosols with concentrations of more than $5 \times 10^2$ up to $10^6$ particles/cm$^3$ are diluted by the dilution air entering annular nozzle 7 in measuring channel 2 connected to measuring volume MV1, particularly in the conical enlargement area 35, for example by a factor of 10 and hence up to a maximum concentration of $10^5$ particles/cm$^3$. These higher concentrations are then measured in measuring volume MV2.

Overall, expansion of the measuring dynamics by a measuring device to a measuring range of less than 1 particle/cm$^3$ up to $10^6$ particles/cm$^3$ is achieved, which is particularly important when, in a stream of gas to be measured, the concentrations change over time or when the separation efficiency of a filter for example is to be determined. Upstream of the filter, the raw gas concentration is usually very high, e.g. up to $10^6$ particles/cm$^3$ in pure gas, so that downstream of the filter the concentration drops to 1 particle/cm$^3$ for example.

What is claimed is:

1. A method of determining the particle size distribution in aerosols in which the particles moving through a measuring channel are detected, said method comprising:
    passing the aerosol through a measuring channel;
    detecting the particle size distribution of the aerosol in a first measuring volume within the measuring channel, the first measuring volume having a cross-sectional area substantially equal to the cross-sectional area of the measuring channel; and
    detecting the particle size distribution of the aerosol in a second measuring volume within the measuring channel and downstream of the first measuring volume, the second measuring volume having a cross-sectional area smaller than the cross-sectional area of the measuring channel and smaller than the cross-sectional area of the first measuring volume.

2. A method according to claim 1, wherein the two measuring volumes are formed by the focal areas of two measuring beams in the measuring channel.

3. A method according to claim 2, wherein the cross-sectional areas of the measuring beams in the focal areas are very different from each other.

4. A method according to claim 2, wherein the cross-sectional areas of the measuring beams in the focal areas differ from each other by at least a power of ten.

5. A method according to claim 2, wherein the cross-sectional area of the first measuring beam in the first focal area is substantially equal to the cross-sectional area of an inlet nozzle for the aerosol and is larger than about $10^{-1}$ mm$^1$, while the cross-sectional area of the second measuring beam in the second focal area is on the order of $10^{-2}$ mm$^2$.

6. A method according to claim 1, wherein the total number of particles flowing through the measuring channel passes through one measuring volume, while only a small number of the particles passes through the other measuring volume.

7. A method according to claim 1, wherein a diluting gas is added to the aerosol to permit measuring of concentrations larger than $10^5$ particles/cm$^3$.

8. A method according claim 7, wherein the diluting gas is conducted to the measuring channel through an annular nozzle which surrounds an inlet nozzle for the aerosol.

9. A method according to claim 7, wherein the diluting gas is supplied to the measuring channel in the area of the first measuring volume.

10. A method according to claim 7, wherein the aerosol is delivered by the diluting gas through the measuring channel.

11. A device for determining the particle size distribution in an aerosol in a measuring channel conducting the aerosols, said device comprising an inlet nozzle for introducing the aerosol into the measuring channel; means in the measuring channel defining a first measuring volume (MV1) located immediately downstream of the inlet nozzle (4) and having a cross-sectional surface perpendicular to the flow direction of the aerosol that corresponds with the surface of the opening of the inlet nozzle; and means in the measuring channel defining a second measuring volume downstream from the first measuring volume and at a distance therefrom, the second measuring volume having a cross-sectional area perpendicular to the flow direction of the aerosol that is smaller than the cross-sectional area of the measuring channel and smaller than the cross-sectional area of the first measuring volume.

12. A device according to claim 11, further comprising measuring optics for irradiating the measuring channel with measuring beams, the measuring beams having focal areas in the measuring volumes.

13. A device according to claim 12, wherein the cross-sectional areas of the measuring beams are very different from each other in the focal areas.

14. A device according to claim 12, wherein the cross-sectional areas of the measuring beams differ from each other in the focal areas by at least a power of ten.

15. A device according to claim 12, wherein the cross-sectional area of the first measuring beam in the first focal area is greater than about $10^{-1}$ $mm^2$. while the cross-sectional area of the second measuring beam in the second focal area is on the order of $10^{-2}$ $mm^2$.

16. A device according to claim 11, wherein all the particles flowing through the measuring channel pass through one of the measuring volumes, while only a small number of the particles pass through the other measuring volume.

17. A device according to claim 1, further comprising a diluting channel (6) terminating in the measuring channel (2).

18. A device according to claim 17, wherein the diluting channel terminates at an annular nozzle located in the measuring channel and surrounding the inlet nozzle.

19. A device according to claim 16, wherein the annular nozzle (7) and inlet nozzle (4) are located immediately upstream of the first measuring volume (MV1).

20. A device according to claim 11, further comprising a common radiation source (L) and a beam splitter creating two measuring beams (9, 11) for the two measuring volumes.

* * * * *